United States Patent [19]
Secrest

[11] Patent Number: 6,055,293
[45] Date of Patent: Apr. 25, 2000

[54] METHOD FOR IDENTIFYING DESIRED FEATURES IN A CRYSTAL

[75] Inventor: Mark Edward Secrest, Vancouver, Wash.

[73] Assignee: Seh America, Inc., Vancouver, Wash.

[21] Appl. No.: 09/108,428

[22] Filed: Jun. 30, 1998

[51] Int. Cl.[7] .................................................. G01N 23/20
[52] U.S. Cl. .............................. 378/70; 378/71; 378/73; 378/76
[58] Field of Search ................................. 378/70, 71, 73, 378/76; 117/14, 902; 428/64.1

[56] References Cited

U.S. PATENT DOCUMENTS

| | | | |
|---|---|---|---|
| 4,634,490 | 1/1987 | Tatsumi et al. | 378/73 |
| 4,710,259 | 12/1987 | Howe et al. | 378/73 |
| 4,771,446 | 9/1988 | Howe et al. | 378/73 |
| 4,788,702 | 11/1988 | Howe et al. | 378/73 |
| 4,862,488 | 8/1989 | Schiller | 378/81 |
| 4,910,758 | 3/1990 | Herrick | 378/71 |
| 4,995,063 | 2/1991 | Enoki et al. | 378/70 |
| 5,073,918 | 12/1991 | Kamon | 378/205 |
| 5,148,457 | 9/1992 | Kubota et al. | 378/70 |
| 5,187,729 | 2/1993 | Ibe et al. | 378/73 |
| 5,720,271 | 2/1998 | Hauser | 125/28 |
| 5,768,335 | 6/1998 | Shahid | 378/73 |
| 5,876,819 | 3/1999 | Kimura et al. | 428/64.1 |

OTHER PUBLICATIONS

B. D. Cullity, Elements of X–Ray Diffraction, second edition (Reading, MA: Addison–Wesley, 1978), p. 233–280, 497–500.

*Primary Examiner*—David P. Porta
*Assistant Examiner*—Allen C. Ho
*Attorney, Agent, or Firm*—Oliff & Berridge, PLC

[57] ABSTRACT

A method for identifying desired features in an off-orientation crystal uses radiation, such as x-rays, directed toward the crystal in a first direction to detect a unique region in a first direction. Based on identifying the unique region, the location of a desired feature, such as a key growth line, is approximated. Radiation is then directed at the crystal in a second direction transverse to the first direction to determine the precise location of the desired feature. The method can be performed automatically by a programmed x-ray device.

23 Claims, 3 Drawing Sheets

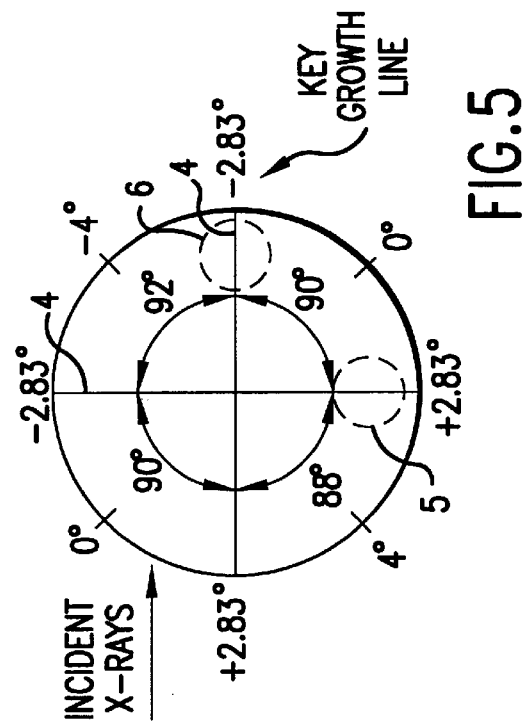
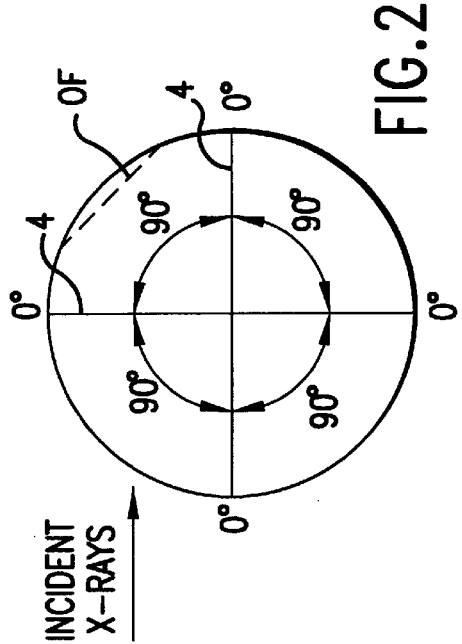
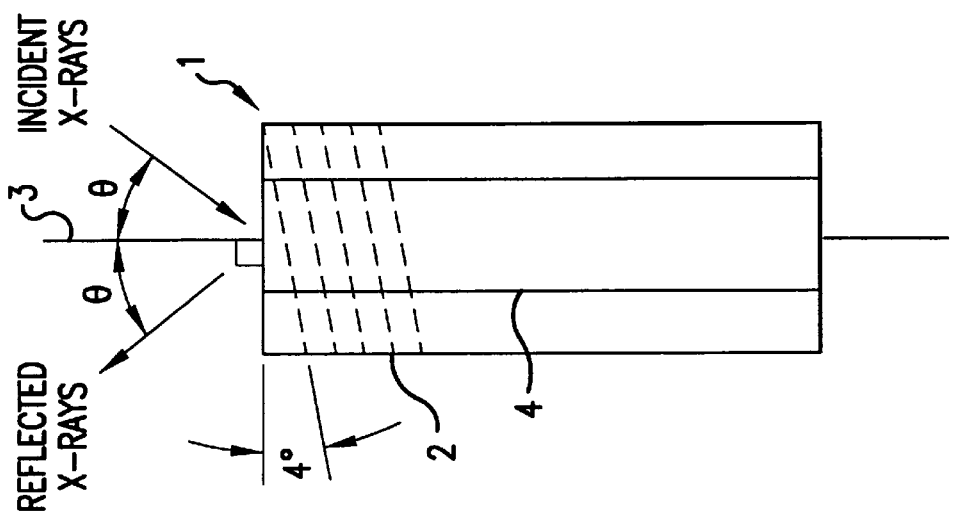
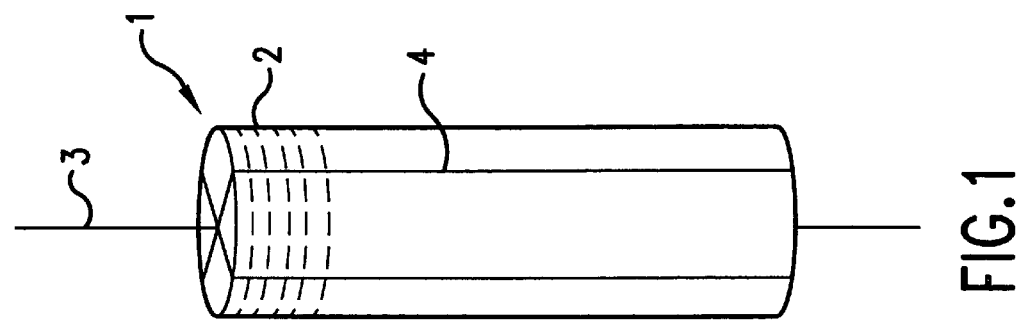

6,055,293

METHOD FOR IDENTIFYING DESIRED FEATURES IN A CRYSTAL

BACKGROUND OF THE INVENTION

1. Field of Invention

This invention generally relates to identifying desired features in a crystal. In particular, the invention relates to a method for identifying desired features in an offorientation crystal using radiation emitted in directions transverse to each other relative to the crystal.

2. Description of Related Art

Single-crystal semiconductor wafers used to produce integrated circuits (ICs) and the like are typically cut from a monocrystalline semiconductor ingot. The semiconductor ingot is typically grown using the Czochralski method whereby a seed crystal is dipped into a semiconductor melt and withdrawn from the melt. As the seed crystal is withdrawn from the semiconductor melt, the semiconductor melt crystallizes to form a roughly cylindrically shaped ingot.

Semiconductor chip manufacturers often require semiconductor wafers having different crystallographic orientations, such as <100> or <111>, which are well known to those of ordinary skill in the art. Since the semiconductor melt that grows from the seed crystal in the Czochralski method has the same crystallographic orientation as the seed, growing an ingot having a desired crystallographic orientation is done mainly by selecting an appropriate seed crystal. Once an ingot of a desired diameter and length has been grown, the end caps of the ingot are removed and the ingot is ground into a cylindrical shape in preparation for cutting wafers from the ingot.

Depending on specific manufacturing requirements, an orientation flat and/or a notch are ground into the ingot at a specific location. The orientation flat and/or notch indicate the relative location of specific crystallographic features, such as habit lines, or nodes, in the ingot that are important to manufacturing ICs and the like.

FIG. 1 shows a side view of a typical ingot 1 that has had its end caps removed and has been ground into a cylindrical shape. The ingot 1 has a <100> crystallographic orientation such that the (100) planes 2 are perpendicular to a longitudinal axis 3 of the ingot 1. Habit lines 4 indicate the crystal orientation and are at 90° intervals around the ingot 1, as shown in an end view of the ingot 1 in FIG. 2.

The crystallographic planes in an ingot 1 are not visible to the naked eye. Therefore, an x-ray goniometer is typically used to determine where crystallographic planes are located in the ingot 1. As is well understood by those of skill in the art, the crystallographic planes are typically found by directing x-ray emission at the ingot 1 and detecting changes in reflection as the ingot 1 is moved. Once a desired crystallographic plane, e.g. a plane or planes associated with a desired habit line 4, is located, an orientation flat OF and/or notch can be ground into the ingot at a desired location, e.g. at an angle of 45° to the habit line 4, as shown in FIG. 2.

Other types of semiconductor ingots, such as <111> ingots, have crystalline structures that require the use of an x-ray goniometer to first identify crystallographic planes in a radial direction relative to the ingot, and then confirm in an axial direction that one of the identified crystallographic plane(s) is acceptable for determining the position of an orientation flat and/or notch in an axial direction relative to the crystal. FIG. 3 shows a schematic end view of a <111> ingot 1. Three of the habit lines 4 (shown in solid lines) are acceptable for orientation flat or other marking location. Three other habit lines (shown in dashed lines) are not acceptable for determining a marking location.

Therefore, the ingot 1 is first illuminated with x-rays in a radial direction to identify (110) planes associated with two habit lines 4. Then, the ingot 1 is illuminated with x-rays in an axial direction. By x-raying in the axial direction, at least one (440) plane associated with one habit line 4 that is acceptable for determining a marking location can be identified. Habit lines 4 that are not appropriate for identifying a marking location do not have an associated detectable (440) plane. Thus, a desired key growth line can be identified, and the ingot 1 appropriately marked with an orientation flat and/or groove or other marking.

Typically, <111> ingots 1 are inspected using two different x-ray machines, i.e. a first x-ray machine is used to inspect the ingot 1 in a radial direction, and the ingot 1 is moved to a second x-ray machine and inspected in an axial direction. A dual x-ray machine has been proposed for inspecting semiconductor ingots that is capable of inspecting an ingot in both the axial and radial directions without removing the ingot 1 from the machine. One type of dual x-ray device is discussed in more detail below in connection with FIG. 7.

In contrast to the on-orientation <100> and <111> ingots discussed above, manufacturing requirements occasionally require that an ingot 1 be prepared off-orientation. For example, FIG. 4 shows a <100> 4° off ingot 1. In contrast to the standard orientation crystal shown in FIG. 1, the 4° off ingot 1 shown in FIG. 4 has its (100) planes 2 at an angle of 4° to a line perpendicular to a longitudinal axis 3 of the ingot 1. As shown in FIG. 5, the habit lines 4 are not evenly spaced around the ingot 1 as in the standard <100> ingot 1. Instead, two of the habit lines 4 are at an 88° angle to each other, and two other habit lines 4 are at a 92° angle to each other.

To determine the location of a key growth line and appropriately mark an ingot 1, an operator typically visually inspects the ingot 1 before the ingot 1 is machined into a cylindrical shape to determine the approximate location of the key growth line. Then, a radial x-ray is used to confirm the precise location of the key growth line. An axial x-ray can be used to confirm that the proper key growth line has been identified. The ingot 1 is then marked with an orientation flat and/or groove or other marking to indicate the crystal feature orientation.

SUMMARY OF THE INVENTION

The invention provides a method for identifying the location of desired features in an off-orientation crystal with high precision and requiring minimal operator visual analysis.

The invention also provides a method of detecting the relative location of a desired feature in an off-orientation crystal comprising the steps of finding a unique region in the crystal by analyzing reflected radiation directed in a first direction toward the crystal; identifying an approximate location of a desired feature relative to the unique region; and determining a precise location of the desired feature by detecting an alternate feature using radiation directed toward the crystal in a second direction.

In one aspect of the invention, the detected alternate feature is the desired feature.

The invention also provides a method of detecting the location of a key growth line in a 40° off-orientation semiconductor crystal whereby a unique region is identified in an axial direction. The approximate location of the key growth line is identified based on the location of the unique region. Then, the precise location of the key growth line is determined by detecting an appropriate (110) plane associated with the key growth line in the radial direction.

In one aspect, the invention provides a step of marking the crystal at a desired location in response to detecting the desired feature.

These and other aspects of the invention will be better understood in connection with the following description of preferred embodiments.

BRIEF DESCRIPTION OF THE DRAWINGS

The invention will be described in relation to the following drawings, in which reference numerals refer to like elements, and wherein:

FIG. 1 shows a schematic side view of a semiconductor crystal ingot;

FIG. 2 shows a schematic end view of the semiconductor crystal ingot of FIG. 1;

FIG. 4 shows a schematic side view of an off-orientation semiconductor crystal ingot;

FIG. 5 shows a schematic end view of the off-orientation semiconductor crystal ingot of FIG. 4;

DETAILED DESCRIPTION OF PREFERRED EMBODIMENTS

The invention is described in relation to identifying features in an off-orientation semiconductor crystal for convenience of reference. However, the invention can be used to detect features in any off-orientation crystal or any other similar object or substance having detectable crystollographic-like or other features. Further, in the following description, planes in a crystal are the detected features. However, the invention can be used to detect other crystal features.

As discussed above, (110) planes associated with habit lines 4 in an on-orienitation <100> crystal ingot 1 can be detected by emitting x-rays toward the ingot 1 in a direction perpendicular to the ingot's longitudinal axis 3, i.e. radially. For example, FIG. 2 shows that incident x-rays are directed from the left toward the ingot 1. As the ingot 1 is rotated about its longitudinal axis 3, changes in the direction and intensity of x-rays reflected by a (110) plane associated with a habit line 4 are detected. Conceptually, one can imagine that the planes in a crystal act like mirrors to reflect the incident x-rays. Thus, as the ingot 1 rotates, x-rays are reflected in different directions and in varying amounts. By detecting the variations in the x-rays reflected by the (110) planes of the ingot 1, the location of the habit lines 4 in the <100> ingot 1 are determined. Once the location of the habit lines 4, or of a single habit line 4 or other features, is determined, the ingot 1 is marked for an orientation flat or notch that indicates the relative location of the habit lines 4 or other desired features.

Unlike the on-orientation <100> ingot 1, which has four equally spaced and crystallographically identical habit lines 4, off-orientation crystals typically do not have evenly spaced or crystallographically identical habit lines 4. For example, as shown in FIG. 5, an off-orientation <100> 4° off ingot 1 has four unique habit lines 4. Two of the habit lines 4 are at 88° with respect to each other, while two other habit lines 4 are at 92° with respect to each other. Accordingly, one cannot simply emit x-rays in a direction perpendicular to the axis 3 of an ingot 1 to identify the location of a desired habit line 4 because once the position of a habit line 4 is located using this method, one cannot be sure which of the four unique habit lines 4 has been identified without careful visual inspection by an operator.

Figure 3:
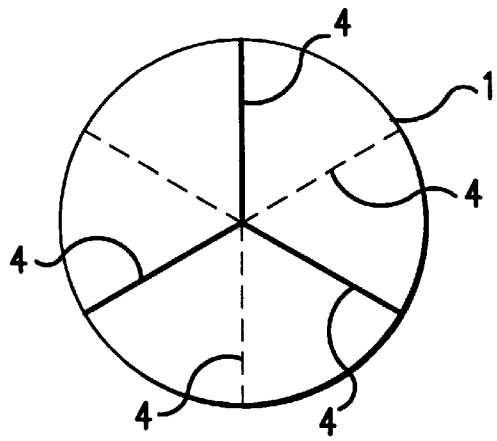
FIG. 3 shows a schematic end view of a <111> crystal ingot.
Figure 6:
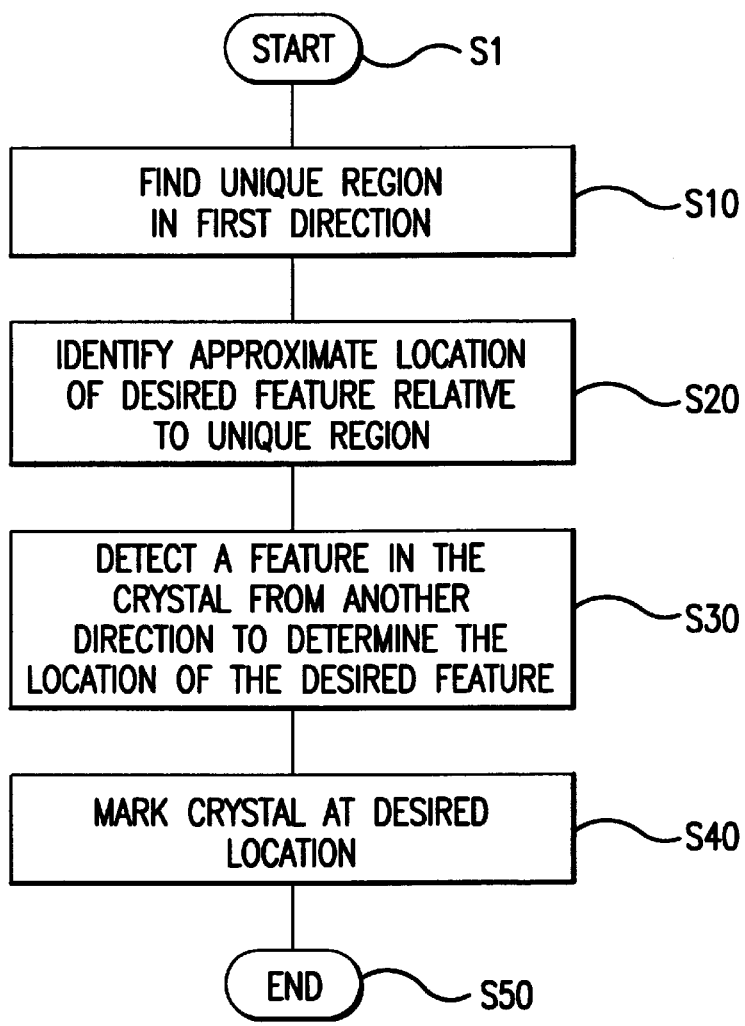
FIG. 6 shows a flow chart of a process for marking a crystal at a desired location to indicate the relative location of a desired feature in a crystal.

A preferred method in accordance with the invention for identifying a key growth line in an off-orientation crystal, such as a <100> 4° off crystal, or for identifying other desired features in an off-orientation crystal, is shown in FIG. 6. In step S10, a unique region in the crystal is identified in a first direction. For the 4° off ingot 1 shown in FIG. 4, x-rays are preferably emitted toward a portion of an end of the ingot 1 in an axial direction at an angle θ to the axis 3, and the reflected x-rays are detected and analyzed. The angle θ is dependent on the desired plane to be located and the material used. The ingot 1 is then rotated a desired amount about its longitudinal axis 3, x-rays are emitted toward a different portion of the end of the ingot 1, and the reflected x-rays are detected and analyzed. The end of the ingot 1 need only be illuminated with x-ray emission twice at two different portions with a known angle preferably perpendicular to each other to identify a unique region of the ingot 1. Of course, the ingot 1 need not be rotated to illuminate the two different end portions. Instead, the two portions could be illuminated without moving the ingot 1 by directing an x-ray beam in two desired directions.

As an example, if the end of the ingot 1 is illuminated at a first portion 5 shown in FIG. 5, the detector will detect that the reflected x-rays represent approximately a +2.83° angle between the (100) planes and a line perpendicular to the longitudinal axis 3. If the ingot 1 is rotated to a second position 90° from the first position to illuminate a second portion 6, the detector will detect approximately a −2.83° angle. Thus, since the crystal structure of the ingot 1 is known to be that shown in FIG. 5, the location of a unique region can be determined, e.g. the unique region having the maximum axial orientation of approximately +4° is located approximately 45° clockwise from the first portion 5. One can be sure that the 92° quadrant opposite the unique region was not identified because the detector would detect approximately a −2.83° angle for both habit lines 4 on either side of the region having a minimum axial orientation of −4°.

The ingot 1 need not be illuminated at two distinct positions to identify the unique region. Instead, x-rays could be constantly directed toward a portion of the end of the ingot 1 as the ingot 1 is rotated about its axis 3. For this example, when the detector detects that the illuminated ingot 1 portion has an axial orientation of approximately 4°, the location of the unique region is identified.

In step S20, since the crystal structure of the ingot 1 and the location of the unique region are known, the approximate location of a desired feature can be identified. In this example, the desired feature is a key growth line that is the first −2.83° habit line 4 positioned counterclockwise from the +4° position on the ingot 1, i.e., the habit line 4 at the 3 o'clock position. Of course, the approximate location of other features, such as desired crystallographic planes or habit lines, could be identified.

In step S30, the ingot 1 is illuminated with x-rays from a direction transverse to the first direction to positively identify the location of the desired feature. In this example, the ingot 1 is preferably rotated about its longitudinal axis 3 while being illuminated with x-rays from a radial direction. Since the approximate location of the key growth line is known, the 4° off ingot 1 is preferably rotated to an approximate position where the radially incident x-rays will detect a (110) plane associated with the key growth line. Then, the ingot 1 is preferably slowly rotated, and when a detectable variation in the reflected x-rays indicates the location of the key growth line, the exact location of the key growth line is determined. In this case, the position of the key growth line is identified by determining variations in x-rays reflected by associated (110) planes in the ingot 1. As will be appreciated by those of skill in the art, other features in the crystal can be used to identify the location of different desired features in the crystal. In some cases, the desired feature may be detected directly, rather than indirectly identifying the location of the desired feature by detecting another feature in the crystal.

In step S40, the crystal is marked at a desired location to indicate the location of the desired feature or features. In this example, an orientation flat or groove could be formed in the ingot 1 at a location 45° in a clockwise direction relative to the location of the key growth line. However, the ingot 1 can be marked in any one or more of many possible locations and in many different ways, such as with a scribe or other non-destructive methods like a marker or paint. Further, the ingot 1 need not be marked at all.

Figure 7:
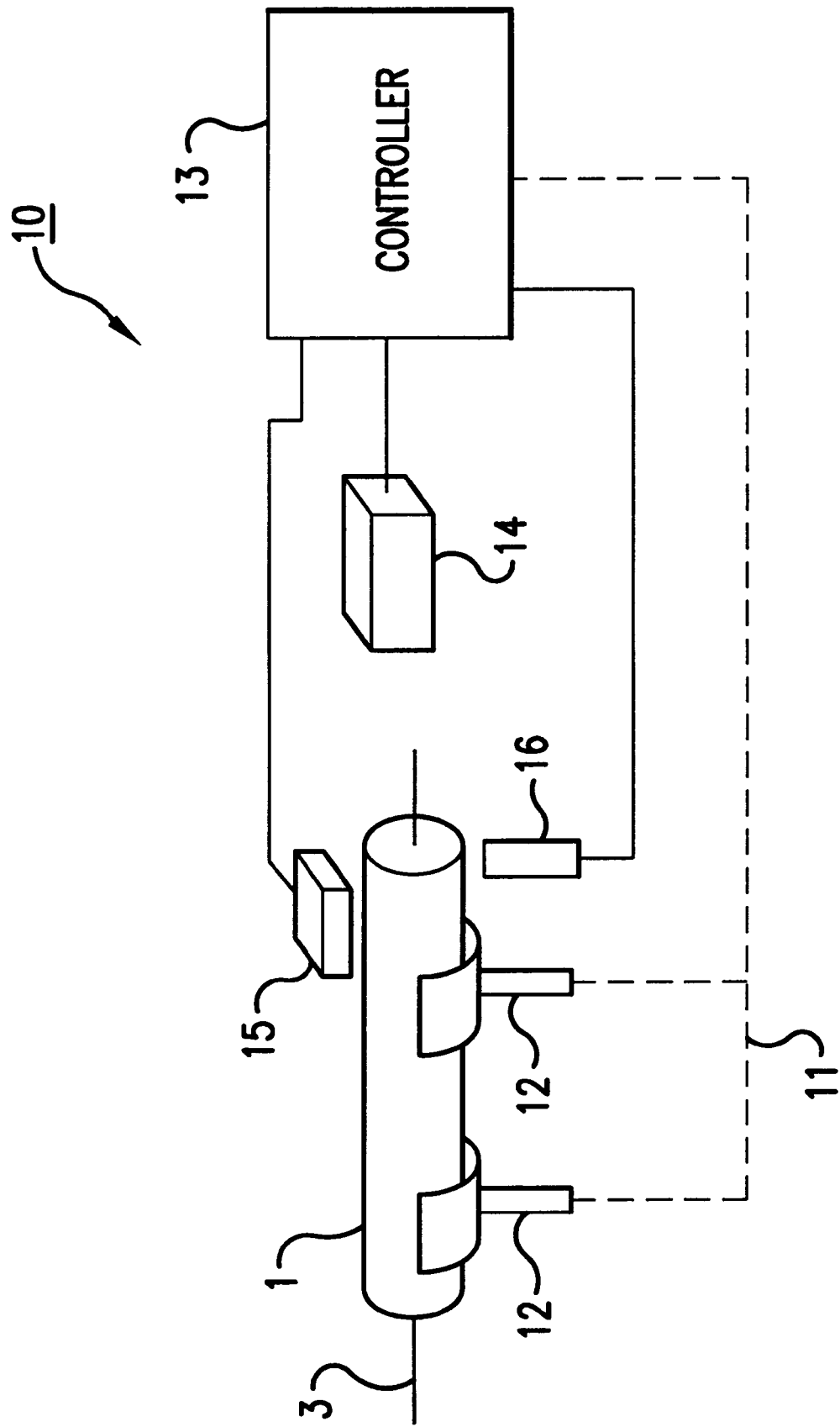
FIG. 7 shows a schematic block diagram of an inspection system.

FIG. 7 shows a semiconductor crystal inspection system 10 that preferably has a pair of ingot supports 12 that hold and control the movement of the ingot 1. Preferably, the ingot supports 12 each have a set of wheels to support the ingot 1 and that are capable of accommodating ingots 1 of different sizes. The wheels are driven by a drive linkage 11 (shown schematically) that is preferably controlled by a controller 13 to rotate the ingot 1 about its longitudinal axis 3.

Although the ingot supports 12 are shown as supporting the ingot 1 from below, the ingot supports 12 could be replaced with a chuck-type device, similar to that used in a conventional lathe, or any other mechanism that can accurately position the ingot 1 around its longitudinal axis 3 and/or an axis perpendicular to the longitudinal axis 3. In addition, the ingot supports 12 or other device should be capable of providing a signal to the controller 13 that is indicative of the amount, direction and/or rate of rotation of the ingot 1, and receive control information from the controller 13 to drive the ingot 1 to a desired location in a desired manner.

The controller 13 also preferably communicates with an axial detector 14 and a side detector 15. The axial and side detectors 14 and 15 each contain an x-ray emission source and x-ray detector. Although the detectors 14 and 15 are shown as single units including both an x-ray emitter and detector, the emitter and detector devices could be physically separated into two devices. Moreover, although x-rays are used in the preferred embodiment to analyze features in the ingot 1, other types of emission, such as gamma rays or electron or other particle emission, can be used. All that is required is that the emission be capable of identifying desired features in the ingot 1 or other object with a desired accuracy and be detectable by some type of detector. Likewise, the detector is preferably an x-ray detector, but can be any type of detector depending of the emission used to identify the crystal features.

Preferably, the system 10 includes a marking device 16 that is controlled by the controller 13 to mark the ingot 1 at a desired location. However, the marking device 16 is not required, since marking could be performed manually by an operator or other device not controlled by the controller 13.

Preferably, the system 10 is programmed to automatically identify a plurality of different features in a plurality of different kinds of crystals. As such, a crystal could be loaded into the system 10, the system 10 instructed as to the type of crystal and desired feature to be identified, and the system 10 could automatically identify the location of the desired feature. Alternatively, the system 10 could determine the type of crystal that is loaded without user or other input, and automatically identify a desired feature in the crystal. The system 10 could also prompt an operator with a list of desired features associated with the crystal that can be located and ask the operator to select at least one feature from the list.

For convenience and clarity, the inspection system 10 is described below as identifying the location of a key growth line in a 4° off ingot 1. However, the system 10 can be used to identify various different features in different types of crystals.

When identifying the location of a key growth line in a 4° off ingot 1, the controller 13 first controls the axial detector 14 to illuminate a portion of an end of the ingot 1 using x-rays directed preferably at an oblique angle to the axis 3 of the ingot 1. Preferably, the detector 14 receives x-rays reflected by the ingot 1 and sends a signal representing the intensity and/or the angle of the received x-rays to the controller 13. Alternatively, the detector 14 could process the information contained in the received x-rays, and output a signal to the controller 13 that indicates that the desired unique region has been identified, for example. Based on the signal from the axial detector 14, the controller 13 determines the angle associated with the illuminated portion of the ingot 1. The controller 13 then controls the ingot supports 12 to rotate the ingot 1 around its axis 3 a predetermined amount, e.g. 90°. The controller 13 then controls the axial detector 14 to again illuminate a portion of the end of the ingot 1. The detector 14 sends another signal representing the angle associated with the second illuminated portion to the controller 13. Alternatively, the ingot 1 could remain stationary and the axial detector 14 moved or the x-ray beam scanned across the end of the ingot 1 to illuminate two different portions of the end. Based on the signals from the axial detector 14 and information regarding the crystal structure that is stored in the controller 13 or otherwise provided, the controller 13 determines the approximate position of the unique region, e.g. the region having the maximum 4° axial orientation.

Alternatively, the controller 13 could control the ingot supports 12 to continuously rotate the ingot 1 as the axial detector 14 "scans" a portion of the end of the ingot 1. The unique region can be identified either by the controller 13 or the axial detector 14 analyzing the information contained in the detected x-rays.

Once the unique region is identified, the controller 13 preferably determines the approximate location of the desired feature based on stored information or information otherwise provided, e.g. by an operator. Alternately, an operator could input the approximate location of the desired feature based on the location of the unique region. Then, the controller 13 controls the ingot supports 12 to rotate the ingot 1 around the axis 3 to a position where the side detector 15 will approximately detect features in the ingot 1 that indicate the location of the desired features or a marking location.

The controller 13 then controls the side detector 15 to illuminate the ingot 1 with x-rays directed in a radial direction, and controls the ingot supports 12 to rotate the ingot 1 around the axis 3. In this example, the location of the key growth line is identified by the side detector 15 illuminating the appropriate (110) planes and providing a signal to the controller 13 that is indicative of the location of the key growth line. When the side detector 15 detects the location of the key growth line, the side detector 15 sends a signal to the controller 13. Based on this signal, the controller 13 determines the precise location of the key growth line and controls the ingot supports 12 to rotate the ingot 1 to a desired location so that the marking device 16 can mark the ingot 1 at the desired location. As discussed above, the inspection system 10 need not mark the ingot 1. Instead, the system 10 could output an indication to an operator where the ingot 1 should be marked or the location of the desired feature.

The inspection system 10 need not have two detectors 14 and 15. Instead, the inspection system 10 could have only one detector, such as the axial detector 14. In this case, the controller 13 could control the axial detector 14 to first identify a unique region on an end of the ingot 1 as described above, and then control the ingot supports 12 to rotate the ingot 1 around an axis perpendicular to the longitudinal axis 3 of the ingot 1. Then, the axial detector 14 could illuminate the ingot 1 with x-rays directed in a radial direction to determine the exact location of the desired feature. Likewise, rather than have the ingot supports 12 rotate the ingot 1 about an axis perpendicular to the longitudinal axis 3, the ingot 1 could remain stationary and the axial detector 14 moved between the axial position shown in FIG. 7 and the side position of the side detector 15 shown in FIG. 7. All that is required is that the system 10 be able to emit x-rays in transverse directions relative to the longitudinal axis 3 of the ingot 1.

Although the examples above only describe identifying a unique region in an axial direction and identifying the location of a desired feature in a radial direction, the invention is not limited to this. Instead, the unique region could be identified in a radial direction and the location of the desired feature identified in an axial direction. Moreover, the directions in which the unique region and location of the desired feature are identified need not be perpendicular. Instead, the unique region and location of the desired feature could be identified in transverse directions that are not necessarily perpendicular, depending on the type of substance being inspected.

The controller 13 can be implemented, at least in part, as a single special purpose integrated circuit (e.g., ASIC) or an array of ASICs, each having a main or central processor section for overall system-level control, and separate sections dedicated to performing various different specific computations, functions and other processes under the control of the central processor section. The controller 13 can also be implemented using a plurality of separate dedicated or programmable integrated or other electronic circuits or devices, e.g., hard wired electronic or logic circuits such as discrete element circuits or programmable logic devices (including PLDs, PLAs, PALs or the like). The controller 13 also includes other circuitry or components, such as memory, relays, mechanical linkages, communications devices, etc. to effect desired control and/or input/output functions.

While the invention has been described with reference to specific embodiments, the description of the specific embodiments is illustrative only and is not to be construed as limiting the scope of the invention. Various other modifications and changes may occur to those skilled in the art without departing from the spirit and scope of the invention as set forth herein.

What is claimed is:

1. A method for determining a location of a target crystallographic feature in an off-orientation crystal, comprising the steps of:

identifying a unique region in the crystal based on detecting at least one alternate crystallographic feature in a first direction;

identifying an approximate location of the target feature based on identifying the unique region; and determining a precise location of the target feature by detecting a crystallographic feature in the crystal in a second direction different from the first direction.

2. The method of claim 1, wherein the step of identifying the unique region comprises the steps of:

illuminating a portion of the crystal with x-rays in the first direction;

detecting x-rays reflected from the illuminated portion;

illuminating a second portion of the crystal with x-rays in the first direction;

detecting x-rays reflected from the second portion; and identifying the unique region based on a result of detection of x-rays reflected from the first and second portions.

3. The method of claim 1, wherein the step of determining a precise location comprises the steps of:

emitting an x-ray beam in the second direction;

moving one of the crystal and the x-ray beam relative to each other about a longitudinal axis of the crystal;

detecting x-rays reflected from the crystal while the crystal is illuminated by the x-ray beam at two different positions; and determining the precise location of the target feature based on a result of detecting the reflected x-rays.

4. The method of claim 1, further comprising the step of rotating the crystal about an axis perpendicular to a longitudinal axis of the crystal prior to determining the precise location of the target feature.

5. The method of claim 1, further comprising the step of moving at least one of an emission source and a detector relative to the crystal prior to determining the precise location of the target feature.

6. The method of claim 1, wherein the unique region is identified in an axial direction relative to the crystal, and the crystallographic feature detected to determine the precise location of the target feature is detected in a radial direction relative to the crystal.

7. The method of claim 1, wherein the unique region is identified in a radial direction relative to the crystal, and the crystallographic feature detected to determine the precise location of the target feature is detected in an axial direction relative to the crystal.

8. The method of claim 1, wherein the step of identifying a unique region comprises the step of controlling a first emission source and detector to identify a first crystallographic feature in the first direction; and the step of determining the precise location of the target feature comprises the step of controlling a second emission source and detector to detect a second crystallographic feature in the second direction.

9. The method of claim 1, wherein the method is automatically performed by a programmed x-ray device.

10. The method of claim 1, wherein the step of identifying an approximate location of the target feature comprises the step of accessing stored crystal feature information.

11. The method of claim 1, wherein the crystal is an off-orientation semiconductor crystal, the unique region is a portion of the crystal that has a maximum axial orientation, the first direction is an axial direction relative to the crystal, the target feature is a key growth line, the second direction is a side direction relative to the crystal, and the crystallographic feature detected in the second direction is at least one (110) plane in the crystal.

12. The method of claim 11, wherein the crystal in a 4° off-orientation semiconductor crystal, and the unique region has an approximately 4° maximum axial orientation.

13. The method of claim 1, further comprising the step of marking the crystal to identify the relative location of the target feature in the crystal.

14. The method of claim 1, wherein the crystallographic feature detected in the second direction is the target feature.

15. A method for determining a location of a key growth line in an off-orientation semiconductor crystal, comprising the steps of:
    identifying a region in the crystal that has a maximum axial orientation in an axial direction;
    identifying an approximate location of the key growth line based on identifying the region; and
    determining a precise location of the key growth line by detecting a feature in the crystal in a radial direction.

16. The method of claim 15, wherein the step of identifying the region comprises the steps of:
    illuminating a first portion of the crystal with x-rays in the axial direction;
    detecting x-rays reflected from the first portion;
    rotating the crystal about a longitudinal axis of the crystal;
    illuminating a second portion of the crystal with x-rays in the axial direction;
    detecting x-rays reflected from the second portion; and
    identifying the region based on a result of detection of x-rays reflected from the first and second portions.

17. The method of claim 15, wherein the step of determining a precise location comprises the steps of:
    emitting x-rays in the radial direction;
    rotating the crystal about a longitudinal axis of the crystal;
    detecting x-rays reflected from the crystal while the crystal is at two different rotational positions; and
    determining the precise location of the key growth line based on a result of detecting the reflected x-rays.

18. The method of claim 15, further comprising the step of moving at least one of an emission source and a detector relative to the crystal prior to determining the precise location of the key growth line.

19. The method of claim 15, wherein the step of identifying a region comprises the step of controlling a first emission source and detector to identify a first feature in the axial direction; and
    the step of determining the precise location of the key growth line comprises the step of controlling a second emission source and detector to detect a second feature in the radial direction.

20. The method of claim 15, wherein the method is automatically performed by a programmed x-ray device.

21. The method of claim 15, wherein the step of identifying an approximate location of the key growth line comprises the step of accessing stored crystal feature information.

22. The method of claim 15, further comprising the step of marking the crystal to identify the relative location of the key growth line in the crystal.

23. The method of claim 15, wherein the crystal in a 4° off-orientation semiconductor crystal, and the region has an approximately 4° maximum axial orientation.

* * * * *